United States Patent
Gagliardi et al.

(10) Patent No.: US 7,786,340 B2
(45) Date of Patent: Aug. 31, 2010

(54) DARK COLORED ABSORBENT ARTICLES WITH LOADING INDICATOR

(75) Inventors: Ivano Gagliardi, Pescara (IT); Giovanna Carlucci, Chieti (IT)

(73) Assignee: The Procter & Gamble Company, Cincinnati, OH (US)

( * ) Notice: Subject to any disclaimer, the term of this patent is extended or adjusted under 35 U.S.C. 154(b) by 2058 days.

(21) Appl. No.: 10/346,962

(22) Filed: Jan. 17, 2003

(65) Prior Publication Data

US 2003/0114809 A1 Jun. 19, 2003

Related U.S. Application Data

(63) Continuation of application No. PCT/US01/22775, filed on Jul. 19, 2001.

(51) Int. Cl.
A61F 13/15 (2006.01)
A61F 13/20 (2006.01)

(52) U.S. Cl. ...................... 604/361; 604/367
(58) Field of Classification Search ............ 604/385.01, 604/361; 428/131
See application file for complete search history.

(56) References Cited

U.S. PATENT DOCUMENTS

| | | | | |
|---|---|---|---|---|
| 4,623,340 A * | 11/1986 | Luceri | ............ | 604/385.05 |
| 4,908,026 A * | 3/1990 | Sukiennik et al. | ............ | 604/378 |
| 5,188,625 A * | 2/1993 | Van Iten et al. | ............ | 604/383 |
| 5,219,341 A * | 6/1993 | Serbiak et al. | ............ | 604/361 |
| 5,437,653 A * | 8/1995 | Gilman et al. | ............ | 604/378 |
| 5,454,800 A * | 10/1995 | Hirt et al. | ............ | 604/378 |
| 5,807,362 A * | 9/1998 | Serbiak et al. | ............ | 604/361 |
| 5,961,505 A * | 10/1999 | Coe et al. | ............ | 604/378 |
| 6,075,178 A | 6/2000 | La Wilhelm | | |
| 6,586,653 B2 * | 7/2003 | Graeme et al. | ............ | 604/375 |
| 6,719,742 B1 * | 4/2004 | McCormack et al. | .. | 604/385.01 |
| 2002/0062115 A1 * | 5/2002 | Wada et al. | ............ | 604/385.23 |
| 2002/0143312 A1 * | 10/2002 | Graeme et al. | ......... | 604/385.01 |
| 2003/0109839 A1 | 6/2003 | Costea et al. | | |
| 2003/0114809 A1 | 6/2003 | Gagliardi et al. | | |
| 2003/0163107 A1 * | 8/2003 | Daskal | ............ | 604/385.01 |
| 2004/0122398 A1 * | 6/2004 | Schnabel et al. | ........ | 604/385.01 |

FOREIGN PATENT DOCUMENTS

| | | |
|---|---|---|
| DE | 297 03 181 U1 | 6/1997 |
| EP | 0 923 919 A1 | 6/1999 |
| EP | 934737 A1 * | 8/1999 |
| EP | 0 951 889 A1 | 10/1999 |
| WO | WO 00/38915 A1 | 7/2000 |

\* cited by examiner

*Primary Examiner*—Melanie J Hand
(74) *Attorney, Agent, or Firm*—Amanda T. Barry; Andrew J. Hagerty; Gary J. Foose (57) ABSTRACT

An absorbent article for absorbing liquid, typically body liquid, with a loading indicator, said article includes a dark topsheet having an L Hunter value of less than 60, preferably being black, an underlying layer comprising a light layer having an L Hunter value of 60 or more and a backsheet, all layers being coextensive to have a common peripheral edge. By this execution the light layer is noticeable along the peripheral edge of the article, thereby providing said loading indicator by changing color to the color of the absorbed liquid.

14 Claims, 3 Drawing Sheets

DARK COLORED ABSORBENT ARTICLES WITH LOADING INDICATOR

CROSS REFERENCE TO RELATED REFERENCES

This is a continuation of International Application PCT/US01/22775 with an International filing date of Jul. 19, 2001.

FIELD OF THE INVENTION

The present invention relates to dark coloured absorbent articles, such as pantiliners or sanitary napkins. More specifically, dark coloured absorbent articles are disclosed comprising a dark coloured topsheet, a backsheet and an underlying layer positioned between the topsheet and the backsheet. All three layers are coextensive. The underlying layer comprises a light coloured layer, which is visible at the peripheral edge of the article. When the article is loaded with body fluids during use the colour of said light layer changes, thereby providing a loading indicator, indicating that the dark coloured article should be substituted by a new one.

BACKGROUND OF THE INVENTION

It has historically been common that absorbent articles, in general including diapers, adult incontinence products, underarm sweat products, collar inserts, sanitary napkins and pantiliners are provided in a colour communicating a hygienic condition. This conventionally resulted in white or predominantly white articles. This did fit well with the historically predominant undergarment colour in which these articles are worn, namely white undergarments. As a result white pantiliners or white sanitary napkins are not easily recognizable when used in such white undergarments.

Very recently fashion has led women more frequently to use other colours than white undergarments. This has been dictated not only by fashion itself but also as a result of the development of clothing, which has a certain translucency and allows the colour of the undergarment to be recognized. Furthermore very recently so-called G-String undergarments or "Tanga-Slips" have become widely used in particular by a younger generation women. These so-called string tangas are particularly used to prevent easy recognition of the contour of the undergarment through tight fitting clothes.

It has thus become a need to have sanitary napkins or pantiliners available, which match the colour of the undergarments (and typically the garments) in order to prevent a colour-based recognition of the presence of such articles (under the assumption that modern clothing can be translucent).

For sanitary napkins or pantiliners having so-called wings which are folded around the outside of the undergarment this is even more important since the wing part of the sanitary napkin or pantiliner is on purpose folded onto the outside of the undergarment and therefore easily visible, depending on the clothing worn over the undergarment.

Sanitary towels comprising an absorbent material and a backsheet (side directed towards the garment), which is skin tone coloured are disclosed in FI 9602361 to Anja Levoranta. The colouring can simulate the real skin colour. DE 19821821 to Evelyn Buetow discloses pantiliners that can be separated in two tanga pantiliners along their diagonal line. They are preferably produced in a variety of different colours. Indeed, the topsheet and the backsheet of these pantiliners might be coloured.

It has been established that in the event that dark coloured absorbent articles are desired, i.e. an article with at least a dark coloured topsheet and preferably both a dark coloured topsheet and backsheet, the problem that arises for the user is how to recognise that the article is loaded and accordingly needs to be changed.

It is thus an object of the present invention to provide a dark coloured absorbent article, namely those having a dark coloured topsheet so as to be designed for use with dark coloured undergarments, typically black ones, that might nevertheless give indication to the user as to when to substitute the article by a new one.

This problem has now been solved by providing absorbent articles with a dark topsheet, a backsheet and an underlying layer, said underlying layer comprising a light layer having an L Hunter value of 60 or more and being positioned between said topsheet and said backsheet, all of those layers being coextensive to have a common peripheral edge.

Because of this particular construction of the absorbent article said light layer is visually detectable along the peripheral edge of the absorbent article, thereby providing a loading indicator by changing colour to the colour of the liquid absorbed within the absorbent article. This is opening the possibility for the wearer to notice by visual inspection along the peripheral edges that the article is loaded with body fluids and to substitute it subsequently.

The absorbent article comprises an underlying layer, which is either a single layer or a multiplicity of layers. The topsheet-facing surface of the underlying layer is preferably of dark colour and more preferably matches the colour of the topsheet. Said topsheet is also preferably apertured, so that the underlying layer, namely the topsheet-facing surface thereof, is visible through the topsheet.

Such an execution is preferred in the context of dark absorbent articles, like pantiliners or sanitary napkins, it is particularly discrete in use when worn with dark coloured undergarment, and is provided with a loading indicator that is discrete too, only serving its purpose of indicating when to change the article.

By said construction, the light coloured layer, typically the absorbent core, is hence not recognizable through the apertures of the topsheet, thereby providing discretion in use of the entire absorbent article of the present invention, but is visible at the peripheral edge of the article, thereby fulfilling its function as a loading indicator. Masking the light coloured layer in dark coloured absorbent articles having a dark apertured topsheet provides enhanced discretion in use, especially in more intimate moment of woman life, where the woman may have to remove her undergarment. Another benefit associated to the dark coloured absorbent articles according to this embodiment of the present invention in use is the masking effect of the bodily discharge absorbed and retained in the absorbent articles. Bodily fluids like vaginal secretions, urine lost and/or menstruation will be masked by the presence of an underlying layer (e.g., secondary topsheet and/or absorbent core) having a topsheet-facing surface with an L Hunter value of less than 60, preferably matching the colour of the topsheet of the absorbent articles of the present invention. This contributes to overall comfort and discretion. Indeed optimum masking of any bodily fluid discharge especially menstrual blood discharge, into the absorbent article, is achieved when both the topsheet and the topsheet-facing surface of the underlying layer have an L hunter value of less than 30 and are preferably of black colour.

In one embodiment herein the absorbent articles of the present invention might comprise in their absorbent core odour control materials like for instance active carbon, which is from far one of the most active and cost effective odour control material. This odour control material was traditionally not desired in conventional hygienic white absorbent articles due to its inherent black colour. Active carbon (also called charcoal) might advantageously be used in the dark coloured absorbent articles of the present invention especially the black ones, without impairing on the comfort and discretion of the article.

In another embodiment of the present invention the underlying layer has a topsheet-facing surface having an L Hunter value of 60 or more. In this execution the underlying layer is noticeable to the wearer of the absorbent article either through apertures of an apertured topsheet, when such a topsheet is incorporated into the article, or through the relative opacity of a non-apertured topsheet, e.g. a thin woven or nonwoven. This underlying layer serves the purpose of a loading indicator as the wearer can notice by visual inspection at the peripheral edge of the article but also through the topsheet that the article has been exposed to body fluids. From an overall discretion point of view this embodiment is less desirable.

SUMMARY OF THE INVENTION

The present invention encompasses an absorbent article for absorbing liquid, typically body liquid, with a loading indicator, said article comprising a dark coloured topsheet having an L Hunter value of less than 60, preferably being black, an underlying layer comprising a light coloured layer having an L Hunter value of 60 or more and a backsheet, all layers being coextensive to have a common peripheral edge. By this execution the light layer is noticeable along the peripheral edge of the article, thereby providing said loading indicator by changing colour to the colour of the absorbed liquid.

BRIEF DESCRIPTION OF THE DRAWINGS

The invention is further described with reference to the accompanying drawings.

DETAILED DESCRIPTION OF THE INVENTION

Definitions

'Absorbent articles' as referred to herein are primarily sanitary napkins, pantiliners, or incontinence pads that are worn in the crotch region of an undergarment. However, articles such as sweat-absorbent underarm pads, nursing pads or collar inserts can also benefit from the present invention. It is even conceivable that baby diapers, adult incontinence diapers, and human waste management devices benefit from the present invention even though they are conventionally not worn in conjunction with an undergarment.

The term 'disposable' is used herein to describe absorbent articles that are not intended to be launched or otherwise restored or reused as absorbent articles (i.e., they are intended to be discarded after a single use and, preferably to be recycled, composted or otherwise disposed of in an environmentally compatible manner).

The term 'topsheet-facing surface' is used herein to describe the surface of a layer being orientated towards the topsheet of the absorbent article. The topsheet of the absorbent article is conventionally orientated towards the wearer's skin.

The term 'backsheet-facing surface' is used herein to describe the surface of a layer being orientated towards the backsheet of the absorbent article. The backsheet of the absorbent article is conventionally orientated towards the wearer's garment.

The absorbent article according to the present invention is conventionally constructed of three main elements: The topsheet, facing the user of the article during use and being liquid pervious in order to allow liquids to pass into the article, the topsheet is preferably an apertured topsheet; the backsheet, providing liquid containment such that absorbed liquid does not leak through the article, this backsheet conventionally provides the garment facing surface of the article; a layer underlying the topsheet, said layer being visible trough the apertures of the topsheet in the event the topsheet is apertured. Preferably such underlying layer consists of a single or multiple layers. The underlying layer has a topsheet-facing surface and a backsheet-facing surface. The underlying layer may comprise a secondary layer also called herein secondary topsheet and/or an absorbent core sandwiched between the topsheet and the backsheet and providing the absorbent capacity of the article to acquire and retain liquid, which has entered the article through the topsheet.

Many absorbent articles and constructions, including particular materials, are known in the art and have been described in ample detail over time. All of such materials are useful in the context of the present invention, provided that they meet the colour requirement as defined herein by the Hunter colour scale values. Typically this will require only moderate modification of the material composition while maintaining the majority of the conventional material characteristics. In the following, examples of materials, which are particularly beneficial for the use in the absorbent articles according to the present invention, are mentioned. Those skilled in the art will readily be able to identify alternative materials, which can also be used in the context of the absorbent articles according to the present invention.

According to the present invention the absorbent article comprises a topsheet, a backsheet and an underlying layer, the topsheet of the absorbent article has an L Hunter value of less than 60, the backsheet preferably has an L Hunter value of less than 60 and the underlying layer comprises a light layer having an L Hunter value of 60 or more. The topsheet, backsheet and the underlying layer are coextensive to have a common peripheral edge.

The L Hunter scale values, utilized herein to define the darkness/lightness of the materials of the absorbent articles according to the present invention, are units of colour measurement in the Hunter Colour system. A complete technical description of the system can be found in an article by R. S. Hunter, 'photoelectric colour difference Meter', Journal of the Optical Society of America, Vol. 48, pp. 985-95, 1958. Devices specially designed for the measurement of colour on the Hunter scales are described in U.S. Pat. No. 3,003,388 to Hunter et al., issued Oct. 10, 1961. In general, Hunter Colour "L" scale values are units of light reflectance measurement, and the higher the value is, the lighter the colour is since a lighter coloured material reflects more light. In particular, in the Hunter Colour system the "L" scale contains 100 equal units of division, absolute black is at the bottom of the scale (L=0) and absolute white is at the top of the scale (L=100). Thus in measuring Hunter Colour values of the materials used in the absorbent articles according to the present invention, the lower the "L" scale value, the darker the material.

The absorbent articles herein, and hence the materials of which the absorbent articles are made of, might be of any colour provided that the L Hunter value defined herein is meet.

'Colour' as referred to herein include any primary colour, i.e., white, black, red, blue, violet, orange, yellow, green, and indigo as well as any declination thereof or mixture thereof.

Colours can be measured according an internationally recognized 3D solid diagram of colours where all colours that are perceived by the human eye are converted into a numerical code. This system is based on three dimensions (x,y,z) and specifically $L^*$, $a^*$, $b^*$.

When a colour is defined according to this system $L^*$ represents lightness (0=black, 100=white), $a^*$ and $b^*$ independently each represent a two colour axis, $a^*$ representing the axis red/green (+a=red, −a=green), while $b^*$ represents the axis yellow/blue (+b=yellow, −b=blue).

Any colour is identified by a unique $\Delta E$ value, which is mathematically expressed by the equation:

$$\Delta E = [(L^*_{ref} - L^*_{sample})^2 + (a^*_{ref} - a^*_{sample})^2 + (b^*_{ref} - b^*_{sample})^2]^{1/2}$$

$\Delta E$ represents graphically the distance between the reference colour and the no colour point (i.e. centre of sphere $L^*_{ref}=50$, $a^*_{ref}=0$, $b^*_{ref}=0$) of the 3d model.

Colour can be measured using the calorimeter MINOLTA mode CR-300 instrument (available from the Minolta Company, Japan) which provides the coordinates $L^*$, $a^*$, $b^*$ and from which the $\Delta E$ value can be determined.

It is to be understood that the L Hunter values and colour values $\Delta E$ considered herein are those measured on the materials of interest (e.g., topsheet or backsheet or underlying layer), taken in layer or folded upon it self, so that upon additional layering of the same material or additional folding thereof, the L Hunter value and colour value stay constant. Indeed the L Hunter value and $\Delta E$ are those of the material per se without any influence of the support onto which the material is disposed in the instrument for its measure. In other words, when measuring the L Hunter value of for example the apertured topsheet layer, several layers of this material are superposed or a layer thereof is folded upon itself several times before measuring its L Hunter value, the same material is measured again after additional layering or folding, this later operation is performed as needed until upon additional layering or folding the L Hunter value does not change any more. This value is the one to be considered herein.

Topsheet

Any conventional topsheet material is used herein provided it meets the L Hunter value defined. Preferred topsheets for use herein are apertured topsheets.

The term apertured topsheet as used herein refers to topsheets having apertures. In general the apertured topsheet is compliant, flexible, soft feeling and non-irritating to the wearer's skin.

Typically the topsheet comprises a plurality of apertures having a pore size of 0.0001 mm to 5 mm. All apertures might have the same dimensions or apertures of different dimensions might be present. The open area of the apertured topsheet is typically from 1% to 50%, preferably from 5% to 45%, more preferably from 10% to 40% and most preferably from 20% to 35%.

The apertured topsheet is typically an apertured polymeric film. Suitable apertured polymeric film topsheets for use herein include polymeric apertured formed films, apertured formed thermoplastic films, apertured plastic films, and hydroformed thermoplastic films; porous foams; reticulated foams; reticulated thermoplastic films; and thermoplastic scrims.

Apertured formed films are particularly suitable for use herein as the apertured topsheet because they are pervious to body exudates and yet non-absorbent and have a reduced tendency to allow fluids to pass back through and rewet the wearer's skin. Thus, the surface of the formed film that is in contact with the body remains dry; thereby reducing body soiling and creating a more comfortable feel for the wearer. Suitable formed films are described in U.S. Pat. No. 3,929,135 (Thompson), issued Dec. 30, 1975; U.S. Pat. No. 4,324,246 (Mullane et al.), issued Apr. 13, 1982; U.S. Pat. No. 4,342,314 (Radel et al.), issued Aug. 3, 1982; U.S. Pat. No. 4,463,045 (Ahr et al.), issued Jul. 31, 1984; and U.S. Pat. No. 5,006,394 (Baird), issued Apr. 9, 1991. Particularly preferred microapertured formed film topsheets are disclosed in U.S. Pat. No. 4,609,518 (Curro et al), issue Sep. 2, 1986 and U.S. Pat. No. 4,629,643 (Curro et al), issued Dec. 16, 1986.

A formed film, which is suitable for use herein, is a black polyethylene apertured formed film, black CPM DH® code 45105/99 available from BP Chemicals, Wasserburg-Germany.

The body surface of the polymeric film topsheet can be hydrophilic so as to help liquid to transfer through the topsheet faster than if the body surface was not hydrophilic. In a preferred embodiment, surfactant is incorporated into the polymeric materials of the formed film topsheet such as is described in PCT Publication No. WO93/09741, "Absorbent Article Having A Nonwoven and Apertured Film Coversheet" filed on Nov. 19, 1991 by Aziz, et al. Alternatively, the body surface of the topsheet can be made hydrophilic by treating it with a surfactant such as is described in the above referenced U.S. Pat. No. 4,950,254.

Other suitable apertured topsheet for use herein are made of woven or nonwoven materials or knit materials. Such materials might be comprised of natural fibres (e.g., wood or cotton fibres), synthetic fibres (e.g., polymeric fibres such as polyester, polypropylene, or polyethylene fibres) or from a combination of natural and synthetic fibres.

Particularly suitable apertured topsheet for use herein are nonwoven topsheet. Suitable nonwoven materials/layers include fibrous nonwoven materials/layers formed by a carding process or a spunbond process or meltblown process whereby molten polymeric material is extruded through a die, attenuated to lengthen the extruded polymer into fibres and decrease the diameter thereof and is subsequently deposited on a forming surface. Methods of forming such nonwoven materials/layers are known to those skilled in the art. Polymeric materials suitable for use in forming such fibrous nonwoven materials/layers include polyolefins such as polyethylene and polypropylene, polyesters, nylons, ethylene vinyl acetate, ethylene methacrylate, copolymers of the above materials, block copolymers such as A-B-A block copolymers of styrene and butadiene, and the like.

A conventional nonwoven material, which is suitable for use herein, is a black spunbonded polyethylene layer commercially available from BBA under code name T27CXC.

Beside the conventional nonwoven materials described herein before, the apertured topsheet for use herein can be made of conventional nonwoven materials typically provided by any process mentioned herein before like spunbond process, into which additional apertures can be formed by any conventional method known to those skilled in the art for this purpose after the nonwoven materials have been formed per se.

Figure 1:
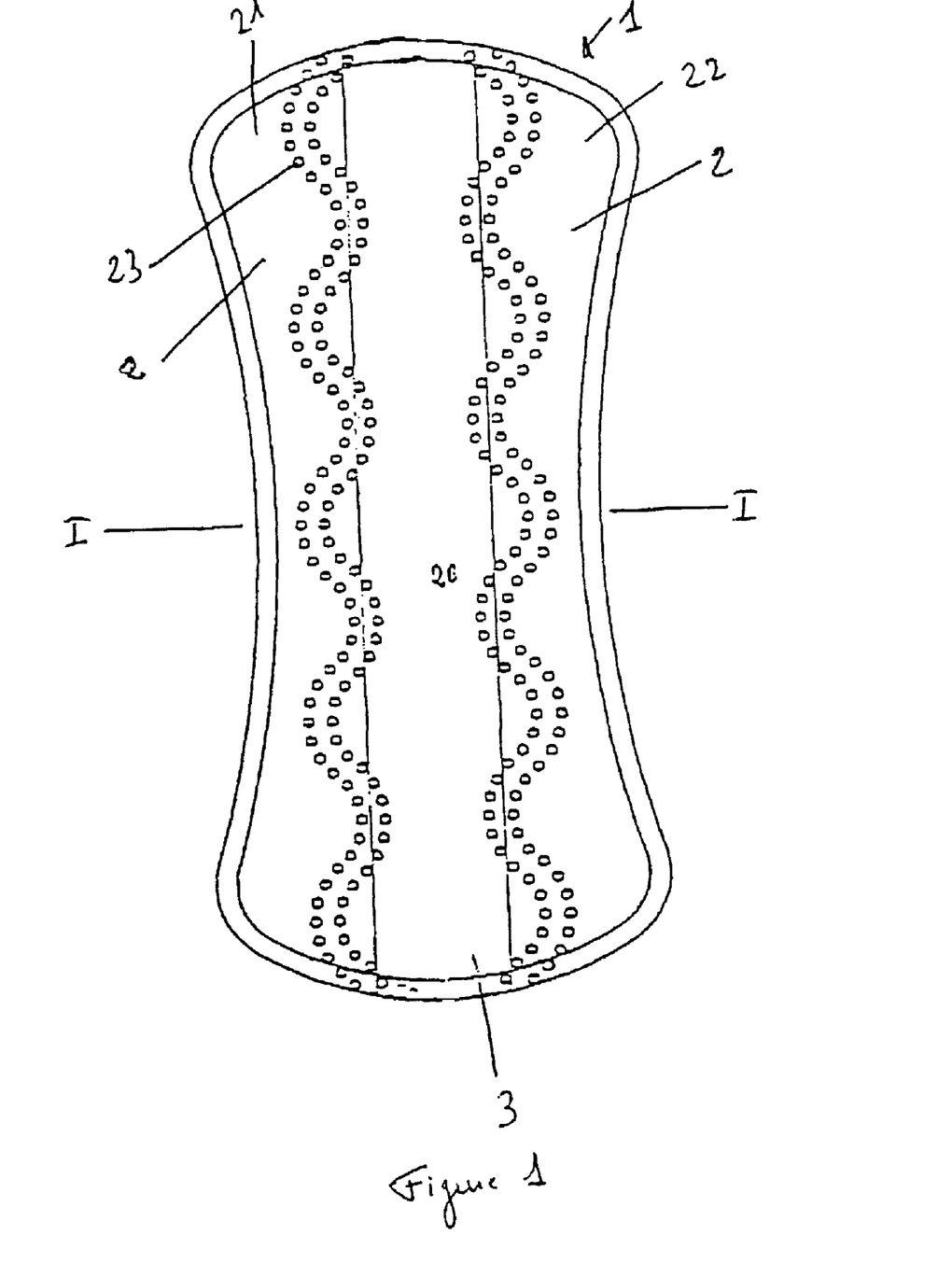
FIG. 1 is a top plan view of a preferred black pantiliner according to the present invention, the topsheet facing the viewer (darkness/colour not shown).

In yet a preferred embodiment herein the apertured topsheet comprises an apertured polymeric film, preferably an apertured formed film, together with a nonwoven outer layer (the nonwoven layer being directed towards the wearer surface). Typically the nonwoven layer is disposed onto the apertured polymeric film in a discontinuous way so that at least the region where liquid is expected to be discharged onto the absorbent article is free of the nonwoven layer. Indeed, it is particularly preferred that the topsheet be a so-called hybrid topsheet in which the wearer contacting surface is provided in its longitudinal centre by an apertured polymeric film while a region not including the centre is provided with a non-woven such as e.g. the high loft non-woven or other non-woven which does provide particularly skin friendliness. Such topsheets have been disclosed in EP-A-523 683, EP-A-523 719, EP-A-612 233, or EP-A-766 953. FIG. 1 illustrates a pantiliner 1 with such a preferred topsheet comprising a nonwoven outer layer 2 and an apertured polymeric formed film layer 3 (apertures not shown). The nonwoven outer layer 2 has an opening 20 positioned in the central zone of the wearer-facing surface of the absorbent article. The opening 20 is provided in the nonwoven outer layer 2 as a passageway for body exudates to be deposited directly onto the apertured formed film layer 3 to take advantage of its superior fluid handling properties so that fluid will rapidly pass into the absorbent core. Typically the nonwoven outer layer 2 comprises two strips 21, 22, spaced apart on top of the apertured formed layer 3 so that the spaced region between the strips 21, 22 forms the opening 20. The two layers can be continuously, partially or intermittently bonded together. In a preferred embodiment the nonwoven outer layer and apertured formed film layer are spot-bonded at a plurality of positions of the strips 21 and 22 with a heat bond 23. The heat bonds 23 provide an embossed seal pattern that can also convey an aesthetic effect in its pattern design, e.g. undulated lines.

The apertured topsheet herein can be made from a nonwoven or woven material or a polymeric film. Such films and nonwovens or wovens can be made for example from polymers such as polyethylene or polypropylene compositions. Conventionally such polymers have been provided with a colouring material such as titanium dioxide to provide a white opacity. Simply using other colouring materials (e.g., dyes, pigments and so on) namely dark colouring materials (like black, navy bleu, grey and the like) provides a dark coloured film or nonwoven. The use of other colouring materials instead of titanium dioxide so as to meet the L Hunter values for the materials to be used herein has the advantage to not cause any substantial material change. Also selecting particular colouring materials to be used in the material from which the topsheet can be made also provides the additional benefit of better material characteristics (besides less costs and a reduced environment burden).

It is to be understood herein that any conventional method known to those skilled in the art to provide a dark coloured topsheet (i.e., material meeting the L Hunter value requirement herein) is suitable for use herein. Dark coloured topsheet can typically be made of any of the materials mentioned above by different methods well known to those skilled in the art, including pigmenting the materials, dying the materials or colour printing the materials.

A preferred example of dark coloured topsheet is a hybrid topsheet with black polyethylene-based apertured formed film CPM DH® code 45105/99 available from BP Chemicals together with black nonwoven spunbonded polyethylene outer layer available from BBA under code name T27CXC. Both these black materials are obtained by using carbon-based pigments.

According to present invention it is highly preferred that the topsheet herein has an L Hunter value of less than 60, preferably less than 45, more preferably less than 30 and most preferably is black. In the embodiment herein wherein different layers are used for the topsheet like an apertured polymeric film layer together with a nonwoven outer layer, all the layers individually match this requirement. Preferably the L Hunter value of the different layers/materials of the topsheet is the same.

In a preferred embodiment the difference in colour value ΔE between different layers/materials of the topsheet, for example between the nonwoven outer layer and the apertured polymeric film layer, is preferably less than 30, more preferably less than 15 and most preferably less than 10. Most preferably the colours of the different layers/materials of the topsheet match each other (are the same (i.e., have same ΔE)).

In a highly preferred embodiment the topsheet is black and is typically provided by using carbon-type pigment as the colouring agent.

It has surprisingly been found that the addition of carbon-type pigments like graphite to nonwoven delivers improved softness to the nonwoven. Without to be bound by theory, it is speculated that this softness benefit is most likely due to the fact that the carbon-type pigment, namely graphite, acts as an impurity, lowering the bonding of polymer base material, thereby delivering a fuzzier finished material which is hence softer at skin contact. Hence in a preferred embodiment of the invention, the absorbent articles have a dark coloured nonwoven topsheet wherein the colour is provided by the presence of carbon-type pigment like graphite. Such absorbent articles having a dark coloured nonwoven topsheet wherein darkness is provided by carbon-type pigment are not only more discrete in use when dark coloured undergarments are considered but also more comfortable.

Backsheet

In general the backsheet is compliant, flexible and soft feeling. The backsheet prevents the exudates absorbed and contained in the absorbent core from wetting clothes that contact the absorbent article such as undergarments. Preferably the backsheet is impervious to liquids (e.g., menses, sweat and/or urine). It can be manufactured from a thin plastic film, although other flexible liquid impervious materials can also be used. As used herein, the term "flexible" refers to materials that are compliant and will readily conform to the general shape and contours of the human body. The backsheet preferably also can have elastic characteristics allowing it to stretch in one or two directions.

The backsheet can comprise a woven or nonwoven material, polymeric films such as thermoplastic films of polyethylene or polypropylene, or composite materials such as a film-coated nonwoven material or fibre-coated film. Conventionally absorbent articles comprise a backsheet of a polyethylene film having a thickness of from about 0.012 mm to about 0.051 mm.

The backsheet is preferably breathable, i.e., allows the transmission of water vapour, or even more preferable the transmission of air, however without sacrificing its main purpose to provide leakage protection for absorbed liquids. The backsheet can also comprise more than one breathable layer so as to replace a single breathable backsheet layer by at least 2 or 3 layers of a different or the same material. In particular two breathable layers forming together the breathable backsheet are preferred.

Preferably the backsheet of the absorbent articles of the present invention has an L Hunter value of less than 60, more preferably less than 40, even more preferably less than 30 and most preferably less than 20. Preferably the difference of L Hunter value $\Delta L$ between the backsheet and the topsheet is less than 20, preferably less than 15 and more preferably less than 10. Preferably the backsheet has the same L Hunter value as the topsheet of the absorbent article.

In a preferred embodiment the difference in colour value $\Delta E$ between the topsheet and the backsheet is less than 40, preferably less than 30, more preferably less than 20 and most preferably less than 15. Typically the backsheet has the same colour (i.e., same $\Delta E$) as the topsheet. In a preferred execution herein the topsheet and the backsheet are black.

According to the present invention a polyethylene backsheet, or in fact any backsheet made from polymeric material can be provided in any colour including dark colour by using a colour filler matching the colour of interest. For instance dark coloured backsheet might be provided by using the suitable among of a colour filler/pigments and preferably a dark colour filler/pigment, instead of the conventional white materials like titanium dioxide. As will be recognized by those skilled in the art the dark colour of the backsheet can be provided in the same manner as in the dark coloured topsheet.

Underlying Layer

The underlying layer can be provided by a single layer/material or by a plurality of layers/materials. Importantly the underlying layer is directly adjacent to the topsheet and thus, in the preferred embodiment herein where the topsheet is apertured, visible through said topsheet. The underlying layer can be provided by any suitable material, including different materials/layers. By 'underlying layer being coextensive with the topsheet and backsheet to have a common peripheral edge' it is meant herein that at least the light layer comprised in the underlying layer is coextensive to the topsheet and backsheet.

The absorbent articles of the present invention comprise as an essential element an underlying layer comprising a light layer having an L Hunter value of 60 or more, preferably more than 70, more preferably more than 80 and most preferably being white. The difference in L Hunter value $\Delta L$ between the topsheet and the light layer of the underlying layer is preferably more than 10, more preferably more than 30 and most preferably more than 45. Because topsheet, backsheet and underlying layer are coextensive, they have a common peripheral edge, where the light layer of the underlying layer is visually detectable. Thereby this light layer serves the purpose of a loading indicator, allowing the user to notice the change of colour due to absorbed body fluids.

In one embodiment of the present invention where the topsheet is preferably apertured the underlying layer might have a topsheet-facing surface having an L Hunter value of 60 or more, preferably the lighter topsheet-facing surface of the underlying layer is visible through the apertures of the darker topsheet. This construction, although not preferred herein due to poor discretion in use, e.g. in the event that an article having a black apertured topsheet is worn together with black undergarment, serves the purpose of a loading indicator not only along the peripheral edge of the article but also through the apertured topsheet when the article was exposed to body fluids.

In a preferred embodiment the underlying layer has a dark coloured topsheet-facing surface having an L Hunter value of less than 60, preferably less than 45 and more preferably less than 30. The difference in L Hunter value $\Delta L$ between the topsheet and the topsheet-facing surface of the underlying layer is typically less than 20, preferably less than 15, more preferably less than 8, even more preferably less than 5, and most preferably less than 3. Preferably the L Hunter value of the topsheet-facing surface of the underlying layer is the same as those of the topsheet or less than the L Hunter value of the topsheet. It is furthermore preferred in this embodiment that the difference in colour value $\Delta E$ between the topsheet and the topsheet-facing surface of the underlying layer is less than 40, preferably less than 30, more preferably less than 20 and most preferably less than 10. In yet a preferred embodiment the colour of the topsheet-facing surface of the underlying layer is the same as those of the topsheet (i.e., same $\Delta E$), preferably black colour.

As for the topsheet any conventional method known to those skilled in the art for providing a dark coloured topsheet-facing surface of the underlying layer is suitable for use herein.

In one embodiment of the present invention the topsheet-facing surface of the underlying layer is provided by a secondary layer (also called secondary topsheet). Such a secondary layer might be manufactured from a wide range of materials such as woven, nonwoven materials, polymeric materials such as apertured formed thermoplastic films, apertured plastic film, hydroformed thermoplastic films, porous foams, reticulated foams, reticulated thermoplastic films and thermoplastic scrims. Any material described herein before for the topsheet can be used for the secondary layer. The secondary layer extends to the periphery of the topsheet so that the secondary layer underlies the topsheet on the entire surface of the topsheet. This secondary layer is positioned between the absorbent core and the topsheet like for example an apertured polymer film and/or nonwoven. Preferably the secondary layer has a L Hunter value of less than 60, more preferably less than 45, even more preferably less than 30 and most preferably the same L Hunter value as the topsheet. In this preferred embodiment the secondary layer is able to mask any further underlying layer whatever its colour, including for example a light coloured absorbent core having an L hunter value of 60 or higher, like conventional white absorbent cores, from being recognized through the topsheet. Advantageously such an absorbent article is able to mask any bodily fluid, especially menstrual fluid, discharged on it and retained on it in the absorbent core. In this execution the underlying layer further comprises as the light layer a light absorbent core. The light coloured core extends to the periphery of the article so that the core underlies the secondary topsheet/layer on the entire surface of the secondary topsheet. In such execution the light coloured core serves the purpose of the light layer comprised by the underlying layer and extends to the periphery of the article and is thus visible on the peripheral edges, thereof underlying the dark coloured topsheet and a dark secondary layer. The light absorbent core visible on the peripheral edges of the article serve as a visual indicator of bodily fluid loading and hence as an indicator of when to change such a dark coloured absorbent article.

A highly preferred secondary layer is a nonwoven secondary layer. The nonwoven secondary layer prevents 'bunching', that is twisting of pantiliner/pad per se, or of the absorbent core in the crotch portion. The inner layer of the apertured topsheet is preferably secured in contacting relation with the nonwoven secondary layer. This contacting relationship results in liquid penetrating the apertured topsheet, preferably the formed film, faster than if the apertured topsheet was not in contact with the secondary layer.

The material of the nonwoven secondary layer can be the same as the nonwoven topsheet described herein before.

In another embodiment the underlying layer is provided by the absorbent core per se in absence of any additional layers between the topsheet and the core. In a preferred embodiment the absorbent core has a topsheet-facing surface having an L Hunter value of less than 60, preferably the same L Hunter value and colour as the topsheet. The backsheet-facing surface of the absorbent core is light and has an L Hunter value of 60 or more, preferably 70 and more preferably 80. The absorbent core extends to the periphery of the topsheet, thereby underlying the topsheet upon its entire surface. The light part of the absorbent core, is thus visible on the peripheral edge of the absorbent article, serving the purpose of a loading indicator.

Absorbent Core

Conventionally the absorbent core can be a single entity or comprise several layers. It can include the following components: (a) optionally a primary fluid distribution layer; (b) optionally a secondary fluid distribution layer; (c) a fluid storage layer; (d) optionally a fibrous layer underlying the storage layer; and (e) other optional components.

a. Optional Primary Fluid Distribution Layer

One optional component of the absorbent core according to the present invention is the primary fluid distribution layer. This primary distribution layer typically underlies the topsheet (if present) and is in fluid communication therewith. The primary distribution layer acquires body fluid for ultimate distribution to the storage layer. This transfer of fluid through the primary distribution layer occurs mainly in the thickness, but may also provide distribution along the longitudinal and transverse directions of the article.

b. Optional Secondary Fluid Distribution Layer

Also optional according to the present invention is a secondary fluid distribution layer. This secondary distribution layer typically underlies the primary distribution layer and is in fluid communication therewith. The purpose of this secondary distribution layer is to readily acquire bodily fluid from the primary distribution layer and distribute it along the longitudinal and transverse directions of the article before transfer to the underlying storage layer. This helps the fluid capacity of the underlying storage layer to be fully utilized.

c. Fluid Storage Layer

Positioned in fluid communication with, and typically underlying the primary or secondary distribution layers, is a fluid storage layer.

The fluid storage layer may be any absorbent means that is capable of absorbing or retaining liquids (e.g., menses and/or urine). The fluid storage layer may be manufactured in a wide variety of sizes and shapes (e.g., rectangular, oval, hourglass, asymmetric, etc.) and from a wide variety of liquid-absorbent materials commonly used in sanitary napkins and other absorbent articles such as comminuted wood pulp that is generally referred to as airfelt. Examples of other suitable absorbent materials include creped cellulose wadding, modified cross-linked cellulose fibres (such as those described in U.S. Pat. No. 5,217,445 issued to Young, et al. on Jun. 8, 1993), capillary channel fibres (that is, fibres having intra-fibre capillary channels such as those described in U.S. Pat. No. 5,200,248 issued to Thompson, et al. on Apr. 6, 1993), absorbent foams (such as those described in U.S. Pat. No. 5,260,345, issued to DesMarais, et al. on Nov. 9, 1993 and U.S. Pat. No. 5,268,244 issued to DesMarais, et al. on Dec. 7, 1993), thermally bonded airlaid materials (such as those material described in U.S. patent application Ser. No. 08/141, 156, entitled "Catamenial Absorbent Structures Having Thermally Bonded Layers For Improved Handling of Menstrual Fluids and Their Use In Catamenial Pads Having Improved Fit and Comfort" filed in the name of Richards, et al. on Oct. 21, 1993), absorbent sponges, synthetic staple fibres, polymeric fibres, hydrogel-forming polymer gelling agents, peat moss, tissue including tissue wraps and tissue laminates, or any equivalent materials or combinations of materials. Suitable fluid storage layers comprising foams are described in European Applications 0 598 833, 0 598 823 and 0 598 834. Suitable fluid storage layers comprising tissue laminates with particles of superabsorbent or gelling agents comprised there between are described in International Patent Applications WO 94/01069 and WO 95/17868.

Preferably the fluid storage layer comprises super-absorbent or gelling materials usually referred to as "hydrogels," "superabsorbent", "hydrocolloid" materials. Absorbent gelling materials are those materials that, upon contact with aqueous fluids, especially body fluids, imbibe such fluids and thus form hydrogels. These absorbent gelling materials are typically capable of absorbing large quantities of aqueous body fluids, and are further capable of retaining such absorbed fluids under moderate pressures. These absorbent gelling materials are typically in a granular form of discrete, non-fibrous particles. However, according to the present invention these super-absorbent gelling materials can also be provided in non-granular form too, preferably in a fibrous form.

In the fluid storage layer these absorbent gelling materials can be dispersed homogeneously or non-homogeneously in a suitable fibrous matrix also referred to as carrier. Suitable carriers include cellulose fibres, in the form of fluff, such as is conventionally utilized in absorbent cores. Modified cellulose fibres such as the stiffened cellulose fibres can also be used. Synthetic fibres can also be used and include those made of cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibres, tricomponent fibres, mixtures thereof and the like. Preferred synthetic and man-made fibres have a denier of from about 3 denier per filament to about 25 denier per filament, more preferably from about 5 denier per filament to about 16 denier per filament. Also preferably, the fibre surfaces are hydrophilic or are treated to be hydrophilic. The storage layer can also include filler materials, such as Perlite, diatomaceous earth, Vermiculite, etc., that lower rewet problems. Further the storage layer may comprise a binder including but not limited to Latex binders, which can be sprayed as an aqueous solution onto the surface of the storage layer prior to curing.

If the absorbent gelling materials are dispersed non-homogeneously in a fibrous matrix, the storage layer can be locally homogeneous, i.e. have a distribution gradient in one or several directions within the dimensions of the storage layer. Non-homogeneous distribution thus includes e.g. laminates of the fibrous carriers enclosing the absorbent gelling materials.

Preferably, the storage layer comprises from 5% to 95% absorbent gelling materials, preferably from 5% to 50%, most preferably from 8% to 35%, absorbent gelling materials. Further the storage layer can comprise from 5% to 95% carrier fibres, preferably from 95% to 50%, most preferably from 92% to 65% carrier fibres.

Suitable absorbent gelling materials for use herein will most often comprise a substantially water-insoluble, slightly crosslinked, partially neutralized, polymeric gelling material. This material forms a hydrogel upon contact with water. Such polymer materials can be prepared from polymerisable, unsaturated, acid-containing monomers. Suitable unsaturated acidic monomers for use in preparing the polymeric absorbent gelling material used in this invention include those listed in U.S. Pat. No. 4,654,039 (Brandt et al), issued Mar. 31, 1987, and reissued as RE 32,649 on Apr. 19, 1988. Preferred monomers include acrylic acid, methacrylic acid, and 2-acrylamido-2-methyl propane sulfonic acid.

Whatever the nature of the basic polymer components of the hydrogel-forming polymeric absorbent gelling materials, such materials will in general be slightly crosslinked. Crosslinking serves to render the hydrogel-forming polymer gelling materials substantially water-insoluble, and crosslinking thus in part determines the gel volume and extractable polymer characteristics of the hydrogels formed from these polymeric gelling materials. Suitable crosslinking agents are well known in the art and include, for example, those described in greater detail in U.S. Pat. No. 4,076,663 (Masuda et al), issued Feb. 28, 1978. Preferred crosslinking agents are the di- or polyesters of unsaturated mono- or polycarboxylic acids with polyols, the bisacrylamides and the di- or triallyl amines. Other preferred crosslinking agents are N,N'-methylenebisacrylamide, trimethylol propane triacrylate and triallyl amine. The crosslinking agent can generally constitute from about 0.001 mole percent to 5 mole percent of the resulting hydrogel-forming polymer material. More preferably, the crosslinking agent will constitute from about 0.01 mole percent to 3 mole percent of the hydrogel-forming polymeric gelling material.

The slightly crosslinked, hydrogel-forming polymeric gelling materials are generally employed in their partially neutralized form. For purposes of the present invention, such materials are considered partially neutralized when at least 25 mole percent, and preferably at least 50 mole percent of monomers used to form the polymer are acid group-containing monomers that have been neutralized with a salt-forming cation. Suitable salt-forming cations include alkali metal, ammonium, substituted ammonium and amines. This percentage of the total monomers utilized, which are neutralized acid group-containing monomers, is referred to herein as the "degree of neutralization."

While these absorbent gelling materials have typically been disclosed in the prior art in granular form, it is possible too in the context of the present invention that the absorbent gelling material is in a non-granular form for example as macrostructures such as fibres, sheets or strips. These macrostructures can be prepared by forming the particulate absorbent gelling material into an aggregate, treating the aggregated material with a suitable crosslinking agent, compacting the treated aggregate to densify it and form a coherent mass, and then curing the compacted aggregate to cause the crosslinking agent to react with the particulate absorbent gelling material to form a composite, porous absorbent macrostructure. Such porous, absorbent macrostructures are disclosed, for example, in U.S. Pat. No. 5,102,597 (Roe et al), issued Apr. 7, 1992.

According to a particularly preferred embodiment of the present invention the absorbent core comprises only one layer, preferably one fluid storage layer.

Any method known to those skilled in the art for colouring materials might be used too for colouring absorbent core, including pigmenting the material, dying the material and/or colour printing the material.

d. Optional Fibrous Layer

An optional component for inclusion in the absorbent cores according to the present invention is a fibrous layer adjacent to, and typically underlying the storage layer. This underlying fibrous layer would typically provide the same function as the secondary fluid distribution layer.

e. Other Optional Components

The absorbent cores according to the present invention can include other optional components normally present in absorbent webs. For example, a reinforcing scrim can be positioned within the respective layers, or between the respective layers, of the absorbent cores. Such reinforcing scrims should be of such configuration as to not form interfacial barriers to fluid transfer, especially if positioned between the respective layers of the absorbent core. Given the structural integrity that usually occurs as a result of thermal bonding, reinforcing scrims are usually not required for the absorbent structures according to the present invention.

Another component, which can be included in the absorbent core according to the invention and preferably is provided close to or as part of the primary or secondary fluid distribution layer are odour control agents. Typically active carbon alone or coated with or in addition to other odour control agents, in particular suitable, zeolite, silica or clay materials, are optionally incorporated in the absorbent core.

Active carbon is the preferred odour control agent for use in the dark coloured absorbent articles according to the present invention like black one, as this material provides outstanding odour control properties at low cost.

Physical Characteristics of Absorbent Cores

Absorbent cores are usually non extensible and non-elastic, however, they can be rendered extensible and depending on the selected materials can also be made to have elastic characteristics. The term "extensible" as used hereinafter refers to a structure, which under external forces such as those occurring during use extends in the direction of the forces or in the direction of a component of the forces in cases where only mono directional extensibility is provided.

The term "elastic" as used hereinafter refers to extensible structures, which return at least partially to their initial state after the forces causing the extension cease to be exerted. Absorbent cores can be corrugated or pleated in one or several directions to provide certain extensibility while selection of elastic fibres for the structure can provide elasticity.

The absorbent cores should preferably be thin. A thickness of less than 5 mm, preferably less than 3 mm, more preferably less than 1.8 mm, and even more preferable between 0.1 and 1.8 mm is desirable such that the resulting articles can also have a low thickness.

Absorbent Article Design

The present invention is particularly applicable to sanitary napkins, panty liners and sweat pads (underarm or collar). A new product design, which is a subform of a sanitary napkin or panty liner form, namely thong shaped sanitary napkins or panty liners, so called thong liners, are particularly susceptible to the present invention. The thong liner design is such that it provides the sanitary napkin or panty liner with a shape such that it can be worn in thong slips, G-string undergarments or string panties; hence the thong shape is fundamentally triangular or trapezoidal.

Optional Components of the Absorbent Articles

Optionally, the absorbent articles of the present invention can comprise all those components typical for the intended product use. For example absorbent articles can comprise components such as wings in order to improve their positioning and soiling protection performance especially towards the rear end of the article. Such designs are shown for example in EP 130 848 or EP 134 086, Thong liners with wings are shown in U.S. design 394,503, UK designs 2,076,491 and 2,087,071 as well as internationally filed industrial model DM 045544, filed under the Hague Agreement, registered on Oct. 21, 1998.

If present the wings preferably match the colour of the remaining article. In fact an article design in which the wings are matching the L Hunter value and preferably colour of the remaining article is preferred. The reason is that wings when folded onto the external side of an undergarment are rather easily visible.

Irrespective whether the wings are specially designed for thong liners or for conventional absorbent articles they can be provided as separate pieces and be attached to the thong liner or conventional pantiliners or sanitary napkins, or they can be integral with the materials of the absorbent articles, e.g. by being integral extension of the topsheet, the backsheet or a combination thereof. If the wings are attached then they can be attached in a basic outward pointing position or already be predisposed towards their in-use position, i.e. towards the longitudinal centreline. If the wings are integral extensions of the topsheet or the backsheet or both then they are provided with the same L Hunter value and preferably colour as these materials.

In general, all typically used components in absorbent products can also be comprised in the absorbent articles according to the present invention as long as the absorbent articles meet the L Hunter value criteria as set in the claims.

Most preferred absorbent articles will comprise a fastening adhesive for attachment. In the case of sanitary napkins, pantiliners or thongliners a so-called panty fastening adhesive is preferred to be present on the backsheet for attachment to an undergarment. However, for sweat pads, e.g. underarm sweat pads, either attachment to an adjacent garment or attachment to the skin of the wearer directly can also be considered. Of course, such direct skin attachment, which is conventionally provided by water gel, hydrogel or oil gel based body adhesives can also be used in sanitary napkins or body liners (in contrast to pantiliners).

EXAMPLES

Examples of pantiliners according to the present invention are as following:

Option 1

Figure 2:
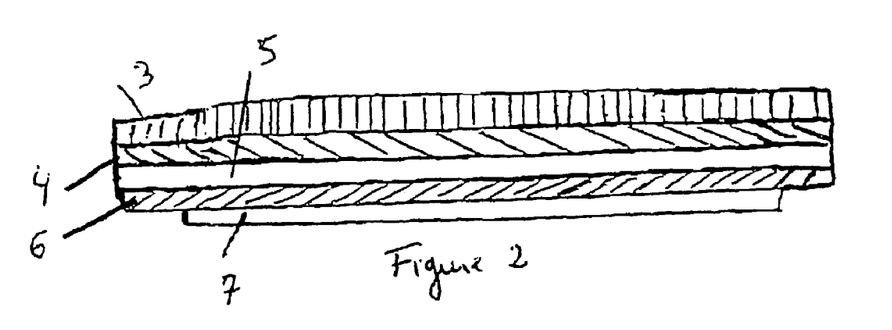
FIG. 2 is an enlarged lateral cross sectional view of a pantiliner according to the present invention.

The pantiliner (as illustrated in FIG. 2) comprises:
as the topsheet, a black apertured polyethylene formed film 3 having holes of 0.2 square millimetres and holes of 1.6 square millimetres, the open area of the apertured formed film being about 32% (black CPM DH®, code name 45105/99 available from BP Chemicals, Germany),
as the underlying layer: —a secondary layer 4 made of black nonwoven spunbonded polyethylene extending on the entire surface of the topsheet (code T27CXC commercially available from BBA, Linotec),
a spiral layer of adhesive (H2128®, available from Ato Findley) (not shown),
a white absorbent tissue core 5 with 10% super absorbent fibres (code GH.100.1008, basis weight 100 gsm commercially available from Concert GmbH, Falkenhagen-Germany), extending to the periphery of the pantiliner,
a spiral layer of adhesive (PM17®, available from Savare) (not shown),
as the backsheet, a polyethylene micro embossed film 6 with black pigments type ST 700 AR0E003171, commercially available from Britton Taco Ltd. Winsford Chesire UK stripes of panty fastening adhesive (HL1461, available from Fuller, Luneburg-Germany)) (not shown) and release paper 7.

Topsheet 3, underlying layer (4 and 5) and backsheet 6 are coextensive to have a common peripheral edge. The white core 5 serves the purpose of a loading indicator.

Option 2

Figure 3:
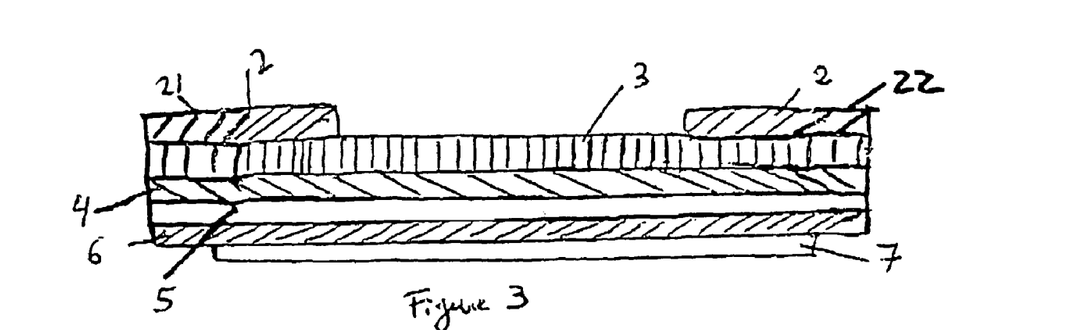
FIG. 3 is an enlarged lateral cross-sectional view taken along line I-I of FIG. 1.

The pantiliner (as illustrated in FIGS. 1 and 3) comprises:
as a topsheet, a black apertured polyethylene formed film 3 having holes of 0.2 square millimeters and holes of 1.6 square millimeters, the open area of the apertured formed film being about 32% (black CPM DH®, code name 45105/99 available from BP Chemicals, Germany), together with black nonwoven spunbonded polyethylene outer layer 2 (code name T27CXC commercially available from BBA, Linotec),
as the underlying layer: —a secondary layer 4 made of black nonwoven spunbonded polyethylene extending on the entire surface of the apertured polyethylene formed film layer 3 (code T27CXC commercially available from BBA, Linotec),
a spiral layer of adhesive (H2128®, available from Ato Findley) (not shown in FIG. 3),
a white absorbent tissue core 5 with 10% super absorbent fibers (code GH.100.1008, basis weight 100 gsm commercially available from Concert GmbH, Falkenhagen-Germany), extending to the periphery of the pantiliner,
a spiral layer of adhesive (PM17®, available from Savare) (not shown in FIG. 3),
as the backsheet, a polyethylene micro embossed film 6 with black pigments type ST 700 AR0E003171, commercially available from Britton Taco Ltd. Winsford Chesire UK,
stripes of panty fastening adhesive (HL1461, available from Fuller, Luneburg-Germany) (not shown in FIG. 3), and release paper 7.

Topsheet 2 and 3, underlying layer 4 and 5 and backsheet 6 are coextensive to have a common peripheral edge. The white core 5 serves the purpose of a loading indicator.

Option 3

Figure 4:
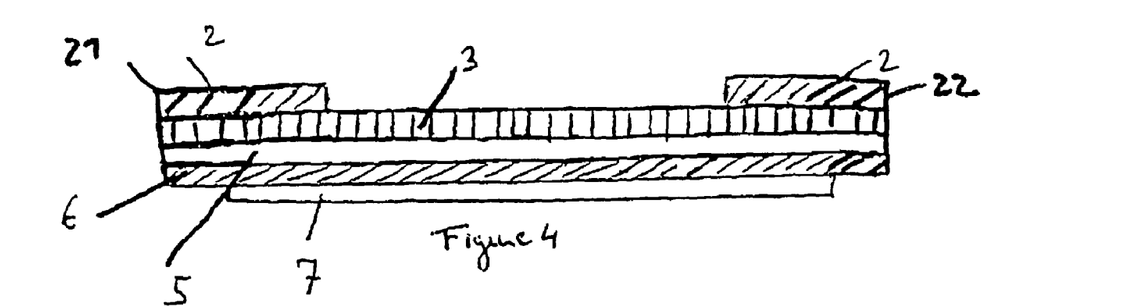
FIG. 4 is an enlarged lateral cross sectional view of another pantiliner according to the present invention.

The pantiliner (as illustrated in FIG. 4) comprises:
as a topsheet, a black apertured polyethylene formed film 3 having holes of 0.2 square millimetres and holes of 1.6 square millimetres, the open area of the apertured formed film being about 32% (black CPM DH®, code name 45105/99 available from BP Chemicals, Germany), together with black nonwoven spunbonded polyethylene outer layer 2 (code name T27CXC commercially available from BBA, Linotec),
the underlying layer is provided by a white absorbent tissue core 5 with 10% super absorbent fibers positioned in the center of the article, the core having a black topsheet-facing surface (different colour of topsheet-facing surface not shown in FIG. 4) and,
a spiral layer of adhesive (PM17®, available from Savare) (not shown in FIG. 4),
as the backsheet, a polyethylene micro embossed film 6 with black pigments type ST 700 AR0E003171, commercially available from Britton Taco Ltd. Winsford Chesire UK,
stripes of panty fastening adhesive (HL1461, available from Fuller, Luneburg-Germany) (not shown in FIG. 4), and release paper 7.

Topsheet 2 and 3, underlying layer 5 and backsheet 6 are coextensive to have a common peripheral edge. The white core 5 serves the purpose of a loading indicator.

Option 4

Figure 5:
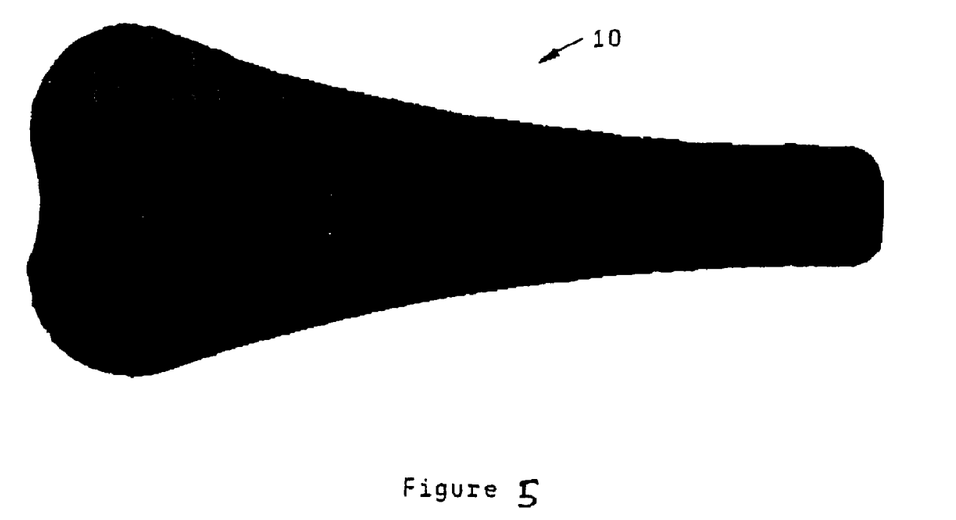
FIG. 5 is a top plan view of another preferred black pantiliner according to the present invention, namely a thong pantiliner, the topsheet facing the viewer.
Figure 6:
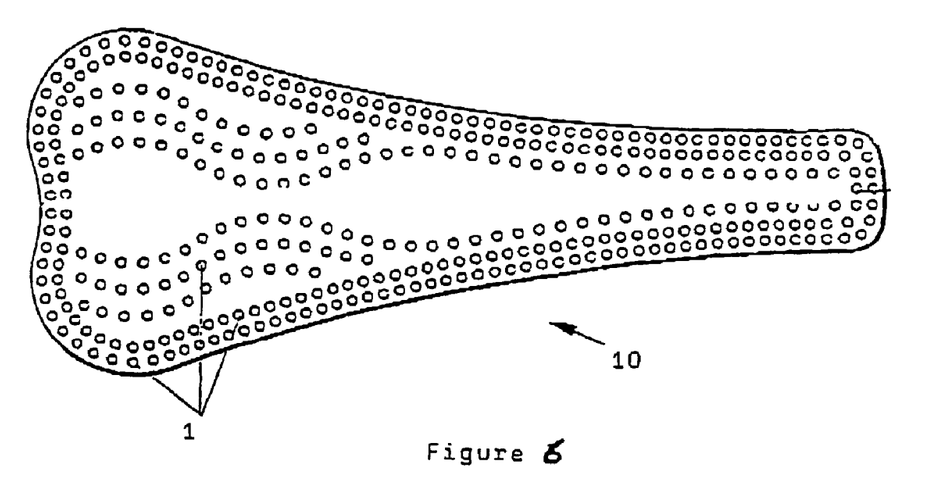
FIG. 6 is a top plan view of a black thong pantiliner according to the present invention, the topsheet facing the viewer, the topsheet being provided with a series of bonding locations 1 at which the topsheet is bonded at least partially to the respective underlying layer in line with the teaching of EP-A-617 602 (darkness/colour not shown).

The thong pantiliner 10 (as illustrated in FIG. 5 or 6) comprises:
- as a topsheet a black nonwoven spunbonded polyethylene extending upon the entire surface of the pantiliner (code name T27CXC commercially available from BBA, Linotec)
- spiral layer of adhesive (code name H2128 available form Ato-Findley)
- as the underlying layer, a full shape one side (topsheet-facing surface) black coloured absorbing tissue core (110 gsm) made of cellulose fibres and synthetic fibres (bico PE/PP) commercially available from Duni under code QTOE 110-PL10065, the backsheet-facing side being white, extending upon the entire surface of the topsheet
- a spiral layer of adhesive (PM17® available from Savare')
- as the backsheet, a polyethylene micro embossed film with black pigments type ST 700 AR0E003171, commercially available from Britton Taco Ltd. Winsford Chesire UK,
- stripes of panty fastening adhesive (HL1461, available from Fuller, Luneburg-Germany) and release paper.

For all the pantiliners exemplified herein before the "black" means an L Hunter value of less than 30, and "white" means an L Hunter value of 70 or more.

The invention claimed is:

1. An absorbent article for absorbing liquid with a loading indicator, comprising a dark coloured topsheet, a backsheet and an underlying layer positioned between said topsheet and said backsheet, wherein said topsheet has an L Hunter value of less than 60, said underlying layer having a topsheet-facing surface and a backsheet-facing surface, wherein said topsheet, said backsheet and said underlying layer are all coextensive to have a common peripheral edge, said underlying layer comprising a light layer having an L Hunter value of 60 or more, said light layer providing said loading indicator.

2. The absorbent article according to claim 1, wherein said topsheet is an apertured topsheet comprising apertures having a pore size from 0.0001 mm to 5 mm.

3. The absorbent article according to claim 2, wherein said topsheet is a nonwoven and/or an apertured polymeric film.

4. The absorbent article according to claim 1, wherein said topsheet preferably has an L Hunter value of less than about 45.

5. The absorbent article according to claim 1, wherein said light layer of said underlying layer preferably has an L Hunter value of more than about 70.

6. The absorbent article according to claim 1, wherein said topsheet-facing surface of said underlying layer has an L Hunter value of less than about 60.

7. The absorbent article according to claim 6, wherein said the difference of L Hunter value ΔL between said topsheet and said topsheet-facing surface of said underlying layer is less than about 20.

8. The absorbent article according to claim 7, wherein said topsheet and said topsheet-facing surface of said underlying layer have the same L Hunter value.

9. The absorbent article according to claim 1, wherein said underlying layer is provided by an absorbent core, comprising a topsheet-facing surface with an L Hunter value of less than about 60 and a light coloured layer with an L Hunter value of about 60 or more.

10. The absorbent article according to claim 1, wherein said underlying layer is provided by a secondary topsheet layer, directly underlying said topsheet and having an L Hunter value of less than about 60, in combination with an absorbent core, directly underlying said secondary topsheet layer and having an L Hunter value of about 60 or more.

11. The absorbent article according to claim 1, wherein the difference of L Hunter value ΔL between said topsheet and said light layer of said underlying layer is more than about 10.

12. The absorbent article according to claim 1, wherein said topsheet-facing surface of said underlying layer has an L Hunter value of about 60.

13. The absorbent article according to claim 1 wherein the backsheet has an L Hunter value of less than about 60.

14. The absorbent article according to claim 1 wherein said article is a sanitary napkin or a pantiliner.

* * * * *